United States Patent [19]
Mignard

[11] Patent Number: 6,146,345
[45] Date of Patent: Nov. 14, 2000

[54] BELT-LIKE SUPPORT DEVICE FOR A PART OF THE HUMAN BODY

[76] Inventor: Jean Louis Laurent Lucien Mignard, 75, rue de la Plage, 62600 Berck-Plage, France

[21] Appl. No.: 09/148,143

[22] Filed: Sep. 4, 1998

[51] Int. Cl.[7] .................................................. A61F 5/00
[52] U.S. Cl. ............................................................ 602/19
[58] Field of Search .............................. 602/18, 19; 2/44, 2/45, 311, 312; 128/99.1, 100.1, 101.1, 96.1; 607/204, 204.15, 204.25, 201, 202, 203

[56] References Cited

U.S. PATENT DOCUMENTS

| | | | |
|---|---|---|---|
| 3,420,230 | 1/1969 | Ballard | 602/19 |
| 4,715,362 | 12/1987 | Scott | 602/19 |
| 4,721,102 | 1/1988 | Pethybridge | 602/19 |
| 5,127,897 | 7/1992 | Roller | 602/19 |
| 5,188,586 | 2/1993 | Castel et al. | 602/19 |
| 5,782,781 | 7/1998 | Nagaoka | 602/19 |
| 5,868,691 | 2/1999 | Vishnevsky | 602/19 |

*Primary Examiner*—Kim M. Lee
*Attorney, Agent, or Firm*—Miles & Stockbridge; Edward J. Kondracki

[57] ABSTRACT

The invention relates to a belt-like support device (1) for a part of the human body comprising at opposite ends (2, 3) complementary fastening elements (4A, 4B) that make it possible to close said belt about a selected part of the body. The support device is characterized in that it longitudinally comprises at least two main complementary bands (5, 6) forming a belt, with each of the main bands having a width less than the width of the belt. The bands (5, 6) may be separated from one another locally.

14 Claims, 4 Drawing Sheets

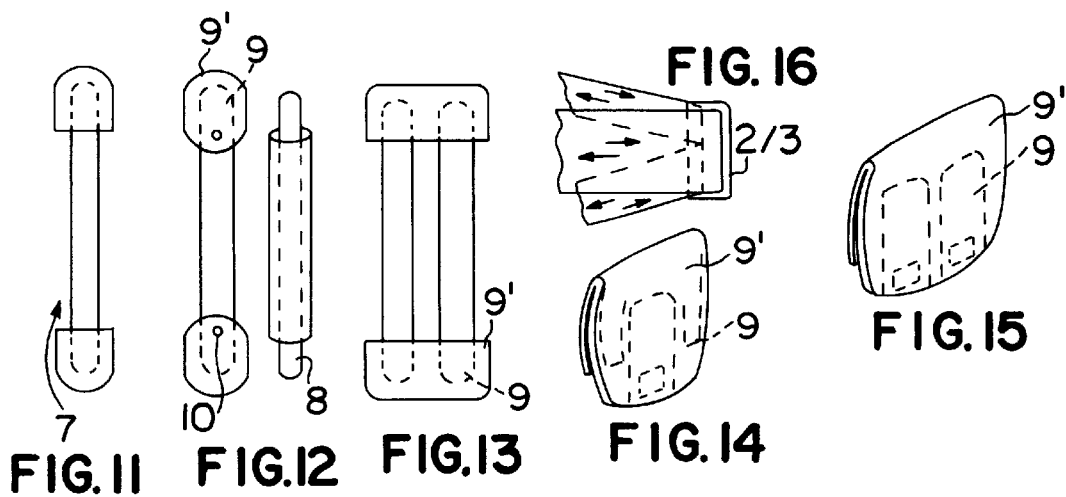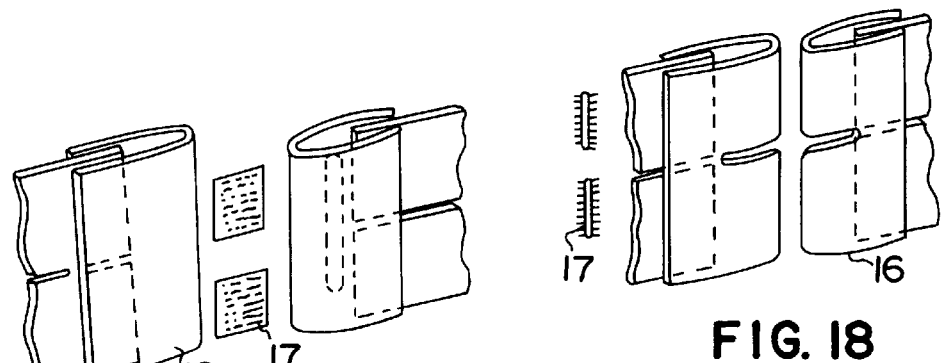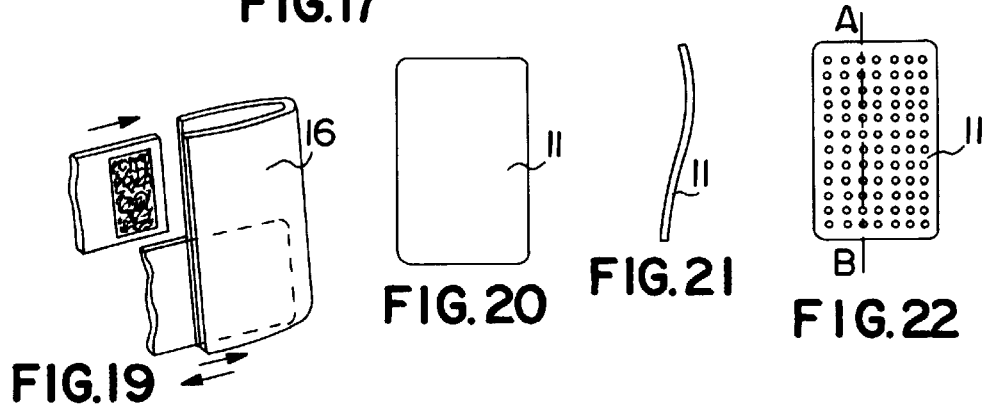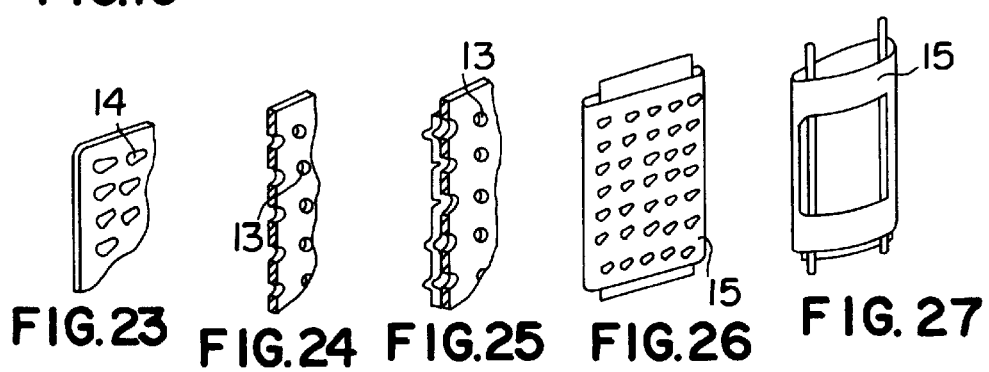

BELT-LIKE SUPPORT DEVICE FOR A PART OF THE HUMAN BODY

FIELD OF THE INVENTION

The invention relates to a belt-like support device for a part of the human body.

DESCRIPTION OF THE RELATED ART

Particularly for lumbar, dorsolumbar, abdominal or sternal support after surgical intervention or in any other case of partial and/or temporary alteration, support belts are often used to relieve the part of the body involved.

For the vertebral column, its sometimes necessary to have both a lumbar support and an abdominal support.

The belts known at the present time essentially comprise a band of generally elastic material having means at each end for fastening the belt at least indirectly to itself, making it possible to adjust the usable length of this belt as a function of the corpulence of the user.

The width of the band of elastic material can be constant, but more generally the width is variable, and most often the belt is wider in the middle part than at its ends.

This belt can be obtained by joining two or three narrower bands whose edges disposed side by side are stitched together to form a single wider band.

It is generally this middle part which is applied to the user's back.

The belts known at the present time are designed to suit individuals whose corpulence falls within a relatively wide range.

Generally, three sizes exist: a small size, a medium size and a large size.

Some belts are capable of being adjusted, but essentially only by playing with the tension of the elastics.

These belts do not make it possible to treat a specific problem for a particular individual as is done in orthopedics, for example like corsets that are made to measure.

SUMMARY OF THE INVENTION

One object of the invention is to obtain a support device that specifically eliminates the above-mentioned drawbacks.

To this end, the subject of the invention is a support device of the above-mentioned type comprising at both of its ends complementary fastening elements which make it possible to close the belt, this belt being characterized in that it longitudinally comprises at least two main complementary bands forming a belt, each of the main bands having a width smaller than the width of the belt, which bands may be separated from each other at least locally.

BRIEF DESCRIPTION OF THE DRAWINGS

The invention will be clearly understood with the aid of the following description, given as a non-limiting example in reference to the appended drawing, which schematically represents:

FIG. 11: a bone or stay in the positioning and attaching pockets, front view, FIG. 12: a front view representing two possibilities for the pockets with the attachment of the bones, FIG. 13: a front view representing a double pocket for positioning and attaching the bones, FIGS. 14 and 15: perspective views of the pockets, FIG. 16: the representation of the adjustments of the two bands relative to the backing and the fastening, the possible directions of positioning and traction, and the relative displacement of the bands from one another, FIG. 17: a buckle fastening, at least one band covered only with hooks on both of its sides allowing the attachment and adjustment of two velour loops, FIG. 18: a variant of FIG. 17 in which the two loops are partially separated horizontally so as to allow another adjustment, FIG. 19: the internal loop/hook adjustment inside the fastening buckle, showing the relative displacement of the bands from one another, FIG. 20: a front view of a panel and/or backing, FIG. 21: a side view of the panel of FIG. 20, FIG. 22: a front view of a panel with perforations, FIG. 23: a view of part of a membrane with hollow fingers;

FIG. 24: a cross section of FIG. 22;

FIG. 25: a cross section of FIG. 22 with certain protuberances pressed into the holes in order to eliminate them, FIG. 26: a membrane surrounding the panel, front view, FIG. 27: a back view of this membrane surrounding the panel and held in place by the bones.

DESCRIPTION OF THE RELATED EMBODIMENTS

Figure 1:
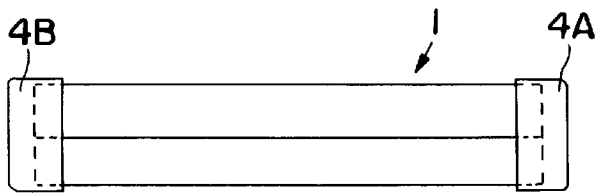
FIG. 1: a first embodiment of the device according to the invention, a schematic front elevation representing a belt comprised of two side-by-side bands held together at each of their ends by the fastening.
Figure 2:
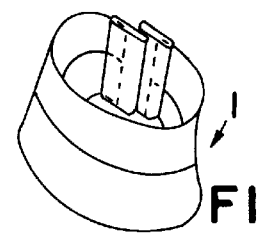
FIG. 2: a rear perspective, belt closed, a view of the schematic front elevation of FIG. 1, FIG. 3: a schematic front elevation, the bands overlapping.
Figure 3:
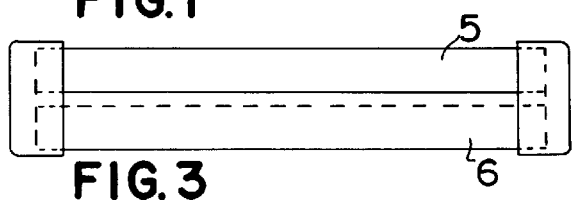
Figure 4:
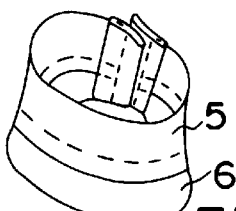
FIG. 4: a rear perspective of FIG. 3, belt closed.
Figure 5:
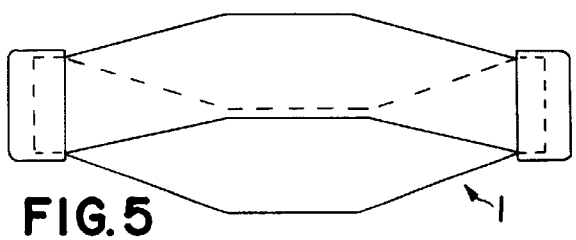
FIG. 5: a schematic front elevation of the bands completely overlapping at each end, partly showing the height that can be obtained by separating the back.
Figure 6:
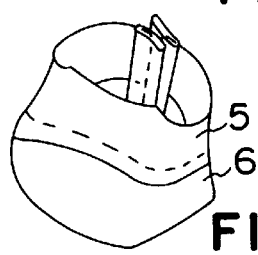
FIG. 6: a rear perspective of FIG. 5, belt closed.
Figure 7:
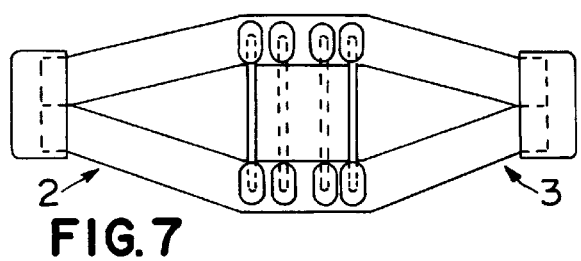
FIG. 7: a schematic front elevation of the bands placed edge-to-edge at each of the fastening ends, the stays or bones maintaining the separation.
Figure 8:
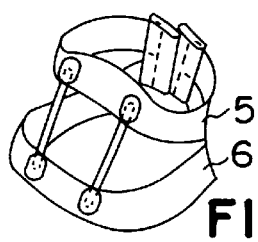
FIG. 8: a perspective of FIG. 7, FIG. 9: a schematic front elevation of the two upper and lower bands held apart by the bones and a center band running from each of the fastening ends and passing over these two bands and the bones.
Figure 9:
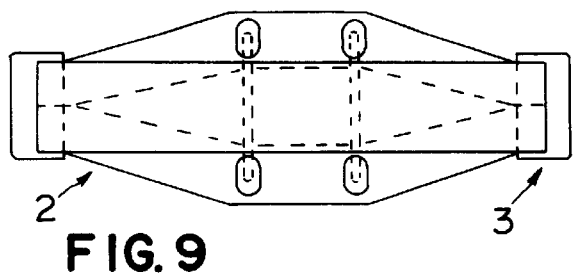
Figure 10:
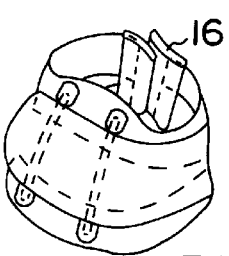
FIG. 10: a perspective of FIG. 9, belt closed.
Figure 28:
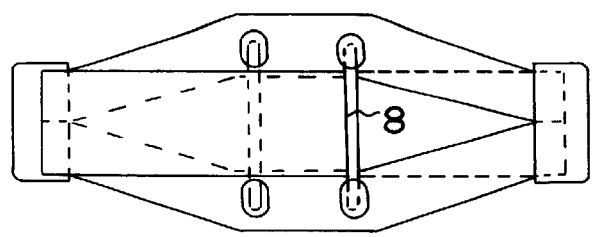
FIG. 28: a schematic front elevation representing the center band passing over one fastening end to which it is attached, and over one stay, then passing under the second stay and under the other fastening end to which it is attached.
Figure 29:
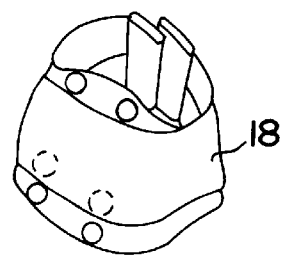
FIG. 29: a perspective, closed belt, with a center band and an exemplary positioning of two pads.
Figure 30:
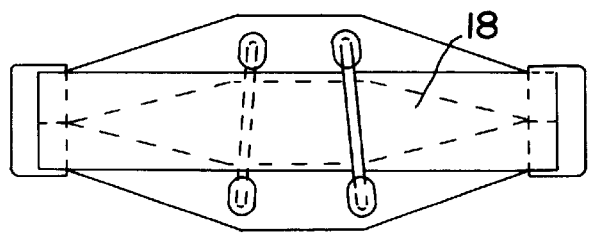
FIG. 30: a schematic front elevation representing the center band running from the top of each fastening end and passing over one stay and under the other.

Referring to the drawings, it may be seen that the support device 1, being in the form of a belt, comprises at both of its ends 2, 3, complementary fastening elements 4A, 4B which make it possible to close this belt.

According to one characteristic of the invention, this support device 1 longitudinally comprises at least two main complementary bands 5, 6 forming a belt, each of the main bands having a width smaller than the width of the belt, which bands 5, 6 are moreover at least locally separated from one another, particularly in order:

either to keep them separate from one another, or to have them overlap each other, or to have them cross each other at least once.

Various combinations resulting from crossing, overlapping or separating are possible.

This belt also has means 7 for holding the bands apart from one another so as to adjust the width of the belt.

For example, the bands 5, 6 are maintained at the required distance by more or less rigid rods 8, such as strips 8 forming bones or stays 8.

If necessary, the rods are covered with a protective sheath.

The bands 5, 6 have means 9 for attaching the ends of the bones, such as pockets 9 into which the ends of the bones 8 are inserted.

The ends of the bones are either simply inserted into the above-mentioned pockets 9, or held in them by fastening means 10 such as a button, a snap, an adhesive or loop/hook fasteners.

It is possible to provide permanent fastening means so that the rods and/or stays are incorporated and irremovable.

These pockets 9 are carried by an added piece 9'.

This added piece 9' comprises one or two pockets 9, or even more.

These rods 8 are substantially vertical and for example parallel to one another or inclined relative to one another, thus forming a V or an inverted V (not shown).

By simply exchanging the bones, for example for longer or shorter bones, it is possible to adjust the support provided to the part of the body involved.

In a variant of embodiment, the bands are maintained at the required distance by at least one panel, hereinafter called a backing 11.

Fastening means 12 make it possible to fasten the backing onto the bands.

These fastening means are preferably designed to make it possible to quickly detach the backing from the bands 5, 6 so that the bands can immediately be positioned differently in order to fulfill a new need.

This fastening can also be designed to be permanent.

The backing is a more or less rigid, heat-formed panel that is malleable whether hot or cold.

This panel could be made of fabric or of stiffer elastic fabric.

The backing is advantageously provided with multiple perforations 13.

In a variant of embodiment, this backing 11 is provided at least locally with protuberances 14 facing the patient's skin for providing a self-massage.

These protuberances 14 are made of a material that is not very compressible, but could also be made of highly compressible material.

They could be, for example, hollow protuberances, substantially in the shape of glove finger ends, attached to one side of a perforated panel, each finger being disposed opposite a perforations 13 in the perforated panel.

Each finger could thus be intentionally retracted by being turned inside-out and inserted through the corresponding hole.

In keeping with their location, these protuberances participate actively in the therapeutic process.

For example, by limiting the number of protuberances to two and positioning them at the level of the sacro-iliac joints.

The protuberances are for example carried by a membrane 15 at least partially surrounding a support.

As a result of its design with two main bands at least locally separated from each other, this belt can thus be adjusted so as to be wider in its middle part or wider at the level of its ends or even laterally.

For this adjustment at the level of the ends, the fastenings that make it possible to buckle the belt could, for example, be carried by a support 16 comprising various positions for attaching the ends of the bands.

This support 16 is attached to the bands by sewing or by other fastening means which allow it to be fastened quickly, such as a snap, etc.

It is advantageous for this support, to which the ends of the above-mentioned bands are attached, to be in the form of support 16 folded in two, between which folds at least some ends of the bands slide and are attached.

It is understood that, as necessary, the bands or at least some of them can be attached to either of the two external surfaces of this edging, whether folded in two or unfolded.

Depending on the placement of the fastenings, the belt can be adapted for right-handed or left-handed persons.

If necessary, this edging 16 is stiffened by at least one short bone.

The fastening of the bands is achieved by fastening means commonly used in orthopedics.

Chiefly, fasteners comprising multiple loops cooperating with multiple hooks of the type known by the trademark "VELCRO" are used.

Advantageously, an intermediate piece 17 provided with hooks on its two opposite sides is used.

Thus, it is very easy to adjust the length of one band relative to the other or to replace one band with another one that is less elastic or more elastic.

For various adjustments which will not be explained below, the bands can also be crossed or interlaced.

The crossover can be used to hold a stay 30.

The bands are at least locally extensible.

In another embodiment, at least one of the bands is inextensible.

In one particular embodiment, one of the bands is extensible but the other is of fixed length.

An elastic material or a fabric in which the weft and/or warp threads are elastic is used.

It can be a synthetic and/or natural material.

It is therefore possible over the course of time to adjust the support by adjusting the settings of the belt without having to remake a customized device each time.

Advantageously, the device comprises a supplementary band 18 added to the existing belt and attached at the level of the two ends of the belt, either permanently or by quick fastening means.

This supplementary band 18 can be placed on the side of the belt in contact with the patient or on the other side.

It includes means for attaching rods or panels which maintain the required distance between the main bands.

Figure 41:
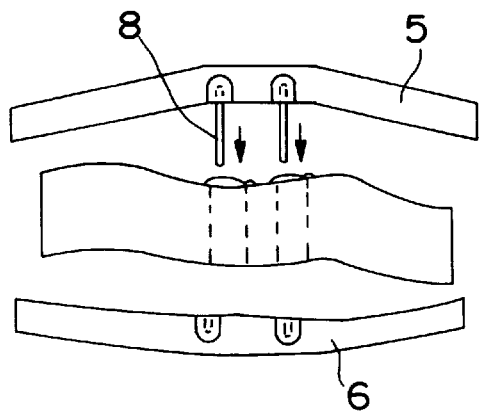
FIG. 41: a detail of the assembly of FIG. 9, FIG. 42: a variant of FIG. 41.
Figure 42:
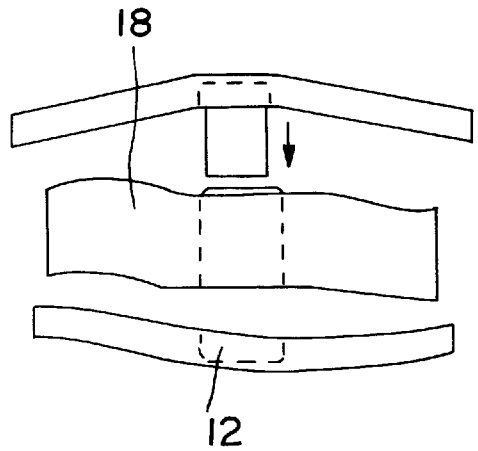

It can also include means for the passage of the rods or panels, through which the latter are inserted (FIGS. 41, 42).

In particular, when the two bands constituting the belt are held apart by the above-mentioned bones, the supplementary band can be deviated at the level of a bone or the edge of the backing, so that part of this supplementary band is located on the inside of the belt and the other part on is located on the outside.

If, contrary to practical experience, the belt is placed on the patient so that the fastening is behind the individual or on his side, an abdominal or lateral support device is obtained.

The support device also comprises shoulder straps and/or even thigh straps (not represented).

One or more hernial pads could also be added.

At least some of the bands have means for attaching accessories such as inflatable pockets 21 or means for electrical or magnetic stimulation.

They can also have sensors making it possible to monitor the electrical activity of the patient.

Advantageously, the support device comprises means for connecting to a back, such as for example the back of a car seat or a corset.

Figure 39:
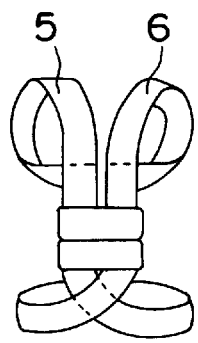
FIG. 39: the two bands with the complete closure positioned for straightening the back.
Figure 40:
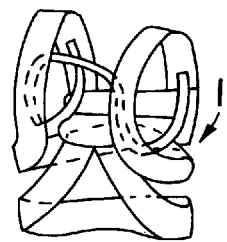
FIG. 40: the two bands with the complete closure positioned on a more or less rigid and/or metal part serving as a sternal support.

Advantageously, while it is commonly used as a belt, this device is perfectly suitable as a back straightener (FIG. 39) or as a sternal support (FIG. 40).

The bands 5, 6 constituting the belt can have variable lengths.

Figure 38:
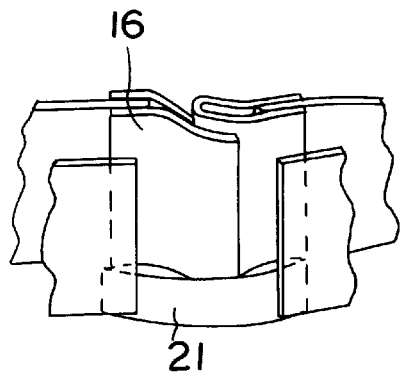
FIG. 38: a front closure with the displacement of the center band toward the bottom in the front, and the positioning of the hypogastric support or strap.

FIG. 38 shows that it is possible to mount on the fastening piece of the belt an additional element forming a hypogastric support 21 which locally supplements, restricts or contains the abdominal wall.

This hypogastric support is held by the center band, which functions as a brace.

Figure 35:
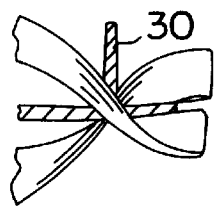
FIG. 35: a positioning relative to a lateral stay in the crossing produced by twisting the two bands.
Figure 31:
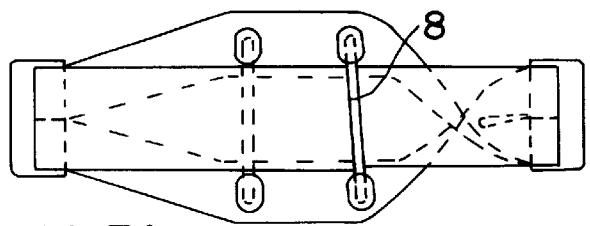
FIG. 31: a schematic front elevation representing the belt with the crossing of the two upper and lower bands, underneath the center band.
Figure 32:
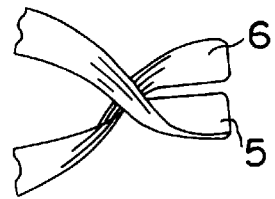
FIG. 32: a detail of the crossing of the two bands.
Figure 33:
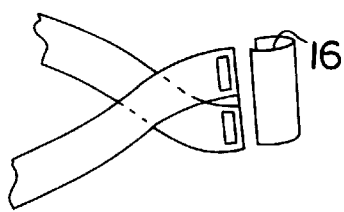
FIG. 33: the two upper and lower bands crossing as a result of the displacement of the ends with the loop/hook fastener inside the fastening buckle.
Figure 36:
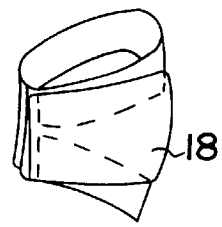
FIG. 36: a side perspective of the belt for abdominal support.
Figure 37:
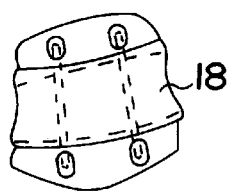
FIG. 37: a side view of FIG. 36 with the separating bones.
Figure 34:
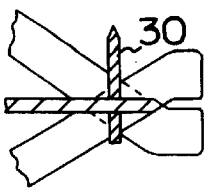
FIG. 34: a positioning relative to a lateral stay in a crossing produced by the loop/hook fastening of the two bands.

FIGS. 34, 35 show the utilization of special stays having anchors or forks which can reinforce all of the paravertebral or backing stays whether connected to them or not, located on the iliac crests, either attached to the belt or sliding through the crossovers of the bands.

This belt comprises means for hanging or attaching pockets filled with a material whose utilization temperature is different from the body of the belt user, for example for treating pain.

While the preferred forms and embodiments of the invention have been illustrated and described, it will be apparent to those of ordinary skill in the art that various changes and modifications may be made without deviating from the inventive concept and spirit of the invention as set forth above, and it is intended by the appended claims to define all such concepts which come within the full scope and true spirit of the invention.

What is claimed is:

1. A belt-like, support device (1) for supporting a portion of the human body comprising a belt having two opposite ends (2,3), said opposite ends (2,3) including complementary fastening closure elements (4A, 4B) for closing said belt (5,6) about the body, said support device further comprising for wrapping about a portion of the body at least two main longitudinal complementary bands forming a belt (5,6), at least one of said bands being locally extensible to form a local band length, each of the main bands having a width smaller than the width of the belt, means for maintaining said bands (5,6) at least locally apart from each other and maintained apart for adjusting the width of the belt, said complementary fastening closure elements (4A, 4B) configured for attaching to said at least one band so as to releasably hold said formed local band length, said fastening closure elements (4A, 4B) including an edging support (16) having various positions configured and arranged to be fastened together for releasably attaching opposite ends of the bands (5,6), whereby said releasable attachment of said opposite ends does not interfere with said releasably held local band length.

2. The support device according to claim 1, characterized in that the bands (5,6) are maintained at a distance apart by rods (8).

3. The support device according to claim 1, characterized in that the bands (5,6) overlap or cross each other.

4. The support device according to claim 3, characterized in that the bands (5,6) include means (9) for attaching opposite ends of the rods (8) to the complementary bands.

5. The support device according to claim 1, characterized in that the edging support to which the ends of the bands (5,6) are attached includes a fold between which fold at least some ends of the bands (5,6) slide and are attached.

6. The support device according to claim 5, characterized in that at least some of the bands are attached to one of two external sides of the edging support (16).

7. The support device according to claim 1, characterized in that at least some of the bands are attached to one of two external sides of the edging support (16).

8. The support device according to claim 1, characterized in that the edging support (16) includes an edging stiffened by at least one short bone.

9. The support device according to claim 1, further comprising a supplementary band (18) added to the belt and attached at the two ends of the belt.

10. The support device according to claim 1, characterized in that at least some of the bands (5,6) have means for attaching accessories.

11. The support device according to claim 1, characterized in that said belt comprises mans for connecting the belt to the back of a seat.

12. A belt support device (1) for supporting a portion the human body comprising a belt having two opposite ends (2,3), said opposite ends (2,3) including complementary fastening closure elements (4A, 4B) for closing said belt (5,6) about the body, said support device further comprising for wrapping about a portion of the body at least two main longitudinal complementary bands forming a belt (5,6), at least one of said bands being locally extensible to form a local band length, each of the main bands having a width smaller than the width of the belt, means for maintaining said bands (5,6) at least locally apart from each other and maintained apart for adjusting the width of the belt, said complementary fastening closure elements (4A, 4B) configured for attaching to said at least one band so as to releasably hold said local band length, the bands (5,6) being maintained in spaced relationship by at least one backing panel (11), said backing panel having means (12) for attaching to the bands (5,6).

13. The support device according to claim 12, characterized in that the backing panel (11) is provided with multiple perforations.

14. The support device according to claim 12, characterized in that the backing (11) panel includes protuberances (14) disposed locally facing a patient's skin for providing a self-massage.

* * * * *